United States Patent

Klingler et al.

[11] 4,214,096
[45] Jul. 22, 1980

[54] NOVEL ISOTHIOURONIUM SALTS

[75] Inventors: Thomas C. Klingler; Ritchie A. Wessling; Dale S. Gibbs, all of Midland, Mich.

[73] Assignee: The Dow Chemical Company, Midland, Mich.

[21] Appl. No.: 48,954

[22] Filed: Jun. 15, 1979

Related U.S. Application Data

[63] Continuation of Ser. No. 569,416, Apr. 18, 1975, abandoned.

[51] Int. Cl.² ............... C07C 157/02; C07C 157/05; C07C 161/00
[52] U.S. Cl. .................... 560/147; 204/181 R; 260/29.6 HN; 260/29.6 MN; 260/29.6 MQ; 260/29.6 SQ; 260/29.6 Z; 260/29.7 SQ; 544/318; 548/300; 560/145; 560/192
[58] Field of Search ............ 544/318; 560/145, 147; 548/300

[56] References Cited

U.S. PATENT DOCUMENTS 3,123,636  3/1964  Loev et al. .................. 260/552
3,721,581  3/1973  Teramura et al. ............. 260/552

Primary Examiner—Vivian Garner

[57] ABSTRACT

Novel isothiouronium salts are herein described which correspond to the formula

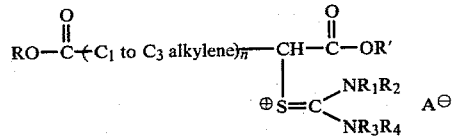

wherein R and R' are each independently hydrocarbyl or inertly-substituted hydrocarbyl of at least 4 carbon atoms; $R_1$–$R_4$ are each independently alkyl or hydroxyalkyl of 1 to 4 carbon atoms, or $R_1$ and $R_3$ are joined to form a 5- or 6-membered heterocyclic ring; n is 0 or 1; and $A^\ominus$ is an inert neutralizing anion. The isothiouronium salts are surprisingly effective dispersing agents and are used in forming electrodepositable latexes.

8 Claims, No Drawings

NOVEL ISOTHIOURONIUM SALTS

CROSS REFERENCE TO RELATED APPLICATION

This is a continuation, of application Ser. No. 569,416 filed Apr. 18, 1975, now abandoned.

BACKGROUND OF THE INVENTION

The terms "thiuronium" and "isothiouronium" appear to be used interchangeably in the art to describe salts formed by reacting a thiourea with an alkylating agent. Such salts will be referred to hereafter as isothiouronium salts.

Loev et al. describe a class of isothiouronium halides which they prepared by reacting an alkylated benzyl halide (e.g., dodecylbenzylchloride) with a N,N,N',N'-tetraalkylthiourea (e.g., N,N,N',N'-tetramethylthiourea). Loev et al indicated that the compounds were useful as surfactants, a property they illustrated by shaking the compounds in water and observing the formation of a foam.

Other isothiouronium salts and methods of preparing same are described by Teramura et al. in U.S. Pat. No. 3,721,581. The isothiouronium salts are there used as flameproofing agents.

SUMMARY OF THE INVENTION

We have discovered a novel class of isothiouroniums which correspond to the formula $$\text{RO}-\overset{\text{O}}{\underset{\|}{\text{C}}}+\text{C}_1 \text{ to C}_3 \text{ alkylene})_{\overline{n}}-\overset{\oplus}{\underset{\underset{\text{S}=\text{C}}{|}}{\text{CH}}}-\overset{\text{O}}{\underset{\|}{\text{C}}}-\text{OR}' \quad \text{A}^{\ominus} \quad \text{I}$$
$$\underset{\text{NR}_3\text{R}_4}{\overset{\text{NR}_1\text{R}_2}{}}$$

wherein:

R and R' are each independently hydrocarbyl or inertly-substituted hydrocarbyl of at least 4 carbon atoms. R and R' are preferably alkyl or alkaryl of from about 6 to about 20 carbon atoms and are most preferably alkyl of from about 6 to about 12 carbon atoms.

$R_1$–$R_4$ are each independently alkyl or hydroxyalkyl of from 1 to 4 carbon atoms, allyl or $R_1$ and $R_3$ are joined to form a 5- or 6-membered heterocyclic ring. Preferably, $R_1$–$R_4$ are each alkyl and are most preferably, each methyl.

The "alkylene" diradical represented by —($C_1$ to $C_3$ alkylene-$)_n$ portion of the molecule may or may not be present, as indicated by the value of n being 0 or 1. Preferably, n is 1 and said alkylene diradical is methylene —($CH_2$)—.

$A^{\ominus}$ is an inert neutralizing anion and may be varied to convenience. By "inert" we mean that the anion is compatible with the cation portion of the compound.

The instant isothiouronium salts are extremely useful surfactants (emulsifiers) and are particularly useful in forming electrodepositable latexes. This fact is illustrated, for example, by the disclosure in U.S. patent application Ser. No. 392,700 filed on Aug. 29, 1973, now Pat. No. 3,882,009, and entitled "Electrodeposition of Isothiouronium Stabilized Lyophobic Colloids" for E. H. Wagner, R. A. Wessling and D. S. Gibbs and the disclosure in their continuation-in-part application Ser. No. 566,865 entitled "Isothiouronium Stabilized Latexes" filed Apr. 10, 1975, now Pat. No. 3,998,776. The disclosures of said applications are incorporated herein by reference.

The instant isothiouronium salts are stable in aqueous media over a wide pH range (e.g. up to about 9 or 10). At pH values above about 9 or 10, the salts tend to decompose. This feature makes them particularly useful in electrodeposition applications in that the latexes containing the instant emulsifiers can be formulated and used at a "neutral" pH (e.g. pH of 6 to 8) but the isothiouronium salt decomposes at the cathode surface (which is a very alkaline environment).

DETAILED DESCRIPTION OF THE INVENTION

The instant isothiouronium salts are conveniently prepared by reacting a dihydrocarbyl α-halodialkanoate corresponding to the formula $$\text{RO}-\overset{\text{O}}{\underset{\|}{\text{C}}}+\text{C}_1 \text{ to C}_3 \text{ alkylene})_{\overline{n}}-\underset{\underset{\text{X}}{|}}{\text{CH}}-\overset{\text{O}}{\underset{\|}{\text{C}}}-\text{OR}' \quad \text{II}$$

wherein R, R' and n have the above meaning and X is chloro, bromo or iodo (more commonly bromo) with an N,N,N', N'-tetra-substituted thiourea corresponding to the formula $$\text{S}=\text{C}\underset{\text{NR}_3\text{R}_4}{\overset{\text{NR}_1\text{R}_2}{\diagup\!\!\!\diagdown}} \quad \text{III,}$$

wherein $R_1$–$R_4$ have the aforesaid meaning. In this reaction, of course, X becomes $A^{\ominus}$ in the product, I. The reaction is normally conducted in a liquid reaction medium as a convenient way of controlling the temperature, facilitating contact between the reactants, etc. The lower alkanols (e.g., methanol, ethanol, etc.) are normally satisfactory in this regard but other conventional solvents could likewise be used. The stoichiometry of the reaction requires 1 mole of III per mole of II. Thus, we normally use a substantially equal molar ratio of reactants in producing our isothiouronium salts but a slight excess of either reactant can be used if desired.

The diesters represented by II above form a class of compounds having many members. Such diesters are conveniently formed by reacting the corresponding α-halodiacid (or acid halide or acid anhydride) with a compound bearing an alcoholic hydroxyl group (i.e. ROH or R'OH). This is a conventional esterification reaction and those skilled in the art will be readily apprised of how to prepare the compounds defined by II. Those skilled in the art will also recognize that some of the esters defined by II can be prepared by reacting the diester of alkenoic diacids (e.g., a diester of maleic acid) with HCl, HBr, etc. Examples of suitable diesters include dibutyl α-chloromalonate, dioctyl α-bromosuccinate, dihexyl α-bromoglutarate, butyl octyl α-iodosuccinate, didodecyl α-iodomalonate, bis(t-butylphenyl) α-bromoglutarate, dicyclohexyl α-bromo-β-methylsuccinate and the like.

The N,N,N',N'-tetra-substituted thioureas also form a known class of compounds which correspond to formula III, above. Such compounds can be formed by reacting thiophosgene with secondary amines in the presence of an acid scavenger. Other preparative methods are likewise known. Examples of suitable such compounds include those of formula III wherein $R_1$–$R_4$ are each methyl, ethyl, propyl, butyl, hydroxymethyl, hydroxyethyl, hydroxybutyl, etc. Suitable such compounds also include those of formula III wherein $R_1$–$R_4$ have different value; e.g. $R_1=R_3=$methyl and $R_2=R_4=$propyl, etc. Five- and six-membered cyclic thioureas are likewise satisfactory reactants and include, for example, N,N'-dimethylethylenethiourea, N,N'-bis(-hydroxymethyl)ethylenethiourea, etc.

The instant isothiouronium salts, I, are useful surfactants (emulsifiers) and are particularly useful in forming electrodepositable latexes, as noted above. Such latexes are oil-in-water dispersions whose average particle sizes normally fall within the range of from about 500 Angstroms to about 10,000 Angstroms. Those compounds within I in which R and R' have a combined carbon content of at least about 16 carbon atoms can also be used to form water-in-oil dispersions.

EXPERIMENTAL

The following examples will further illustrate the invention.

EXAMPLE 1

Preparation of [1,4-bis(butoxy)-1,4-dioxobutane-2-yl][bis(dimethylamino)methylene]sulfonium bromide A solution of dibutyl α-bromosuccinate (100 g.; 0.324 mol) and N,N,N',N'-tetramethylthiourea in 300 ml. of methanol was warmed at reflux temperature for five hours. The reaction mixture was extracted twice with 250 ml. portions of n-hexane to remove unreacted starting materials and the methanol layer containing the product was isolated and recovered. The methanol was removed therefrom under reduced pressure to give 135.9 g. of an amber oil which solidified upon standing. This material was dissolved in water and the aqueous solution extracted with diethyl ether to yield an aqueous solution of the isothiouronium salt. The nuclear magnetic resonance spectrum of the product was consistent with the following structure

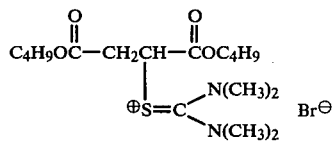

EXAMPLES 2–5

The following isothiouronium salts were prepared in like manner except for the α-bromosuccinate diester used. The compounds were all produced in excellent yields. The results are summarized in Table I.

Table I

| Ex. | Product Structure |
|---|---|
| 2 | $C_4H_9OC(O)CH_2$—CHY—$C(O)OC_6H_9$ |
| 3 | $C_8H_{17}OC(O)CH_2$—CHY—$C(O)OC_8H_{17}$ |
| 4 | $CH_3(CH_2)_3CHCH_2OC(O)$—$CH_2$—CH—$C(O)OCH_2CH(CH_2)_3CH_3$<br>           $\mid$                      $\mid$                         $\mid$<br>          $C_2H_5$                   Y                  $C_2H_5$ |
| 5 | $C_9H_{19}C_6H_4OC(O)CH_2$—CHY—$C(O)OC_6H_4C_9H_{19}$ |

In each of Examples 2–5 in Table I, "Y" in the product formula means

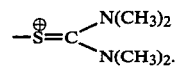

Other isothiouronium salts can be similarly prepared by merely varying the reactants. The anion associated with the above isothiouronium salts can be changed by using, for example, the α-chlorosuccinate instead of the α-bromosuccinates or, alternatively the anion can be changed by conventional anion exchange techniques. For example, the anion could thus be changed to iodide, bisulfate, nitrate, bicarbonate, dihydrogen phosphate, acetate, p-toluenesulfonate, benzoate, etc.

EXAMPLE 6

This experiment illustrates the utility of the instant thiouronium salts in forming oil-in-water emulsions. The product of Example 3 (5 g.) was diluted to 300 grams with deionized water. This was charged to a reactor vessel equipped with a mechanical stirrer, a nitrogen bleed stream, condenser, and heating means. Azobisisobutyronitrile (3 g.), butyl acrylate (60 g.), styrene (40 g.) and dodecanethiol (0.1 g.) were then added to the reaction vessel under a nitrogen blanket. The reaction mixture was heated under nitrogen to 70° C. and maintained at that temperature for eight hours with continual stirring. At the end of this time, we recovered a clear, fluid latex having 25 weight percent solid content (representing a 99 percent conversion). The average particle size was 905 Angstroms. The latex was an electrodepositable latex and, when used according to the procedure described by Wagener et al., supra, the latex gave a smooth, dry film on a zinc phosphate coated steel cathode (Bonderite ® EP-2). There was no "sulfur odor" on either the coated panel or in the latex bath. This lack of odor is a surprising feature of the instant isothiouronium salts.

We claim:

1. A surfactant corresponding to the formula

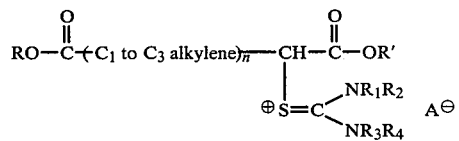

wherein:

R and R' are each independently alkyl or alkaryl groups of from about 4 to about 20 carbon atoms;

$R_1$, $R_2$, $R_3$ and $R_4$ are each independently alkyl or hydroxyalkyl of from 1 to 4 carbon atoms, allyl or $R_1$ and $R_3$ are part of a single ethylene or propylene moiety which joins the two nitrogen atoms to form a 5- or 6-membered cyclic thiourea;

n is 0 or 1;

$A^{\ominus}$ is an anion.

2. The compound defined by claim 1 wherein R and R' are alkyl groups of from about 6 to about 12 carbon atoms.

3. The compound defined by claim 2 wherein $R_1$–$R_4$ are each methyl.

4. The compound defined by claim 1 wherein $R_1$–$R_4$ are each alkyl.

5. The compound defined by claim 4 wherein $R_1$–$R_4$ are each methyl.

6. The compound defined by claim 5 wherein R and R' are each butyl, hexyl, octyl or nonylphenyl.

7. The compound defined by claim 6 wherein R and R' are each octyl.

8. The compound defined by claim 7 wherein $A^{\ominus}$ is $Br^{\ominus}$.

* * * * *